United States Patent
Eddie (10) Patent No.: US 11,845,082 B1
(45) Date of Patent: Dec. 19, 2023

(54) SPECIMEN TUBE

(71) Applicant: Amazon Technologies, Inc., Seattle, WA (US)

(72) Inventor: Justinn Eddie, Cincinnati, OH (US)

(73) Assignee: Amazon Technologies, Inc., Seattle, WA (US)

( * ) Notice: Subject to any disclaimer, the term of this patent is extended or adjusted under 35 U.S.C. 154(b) by 245 days.

(21) Appl. No.: 17/212,905

(22) Filed: Mar. 25, 2021

(51) Int. Cl.
*B01L 3/00* (2006.01)
*G01N 33/52* (2006.01)
*G01N 1/00* (2006.01)

(52) U.S. Cl.
CPC .......... *B01L 3/5082* (2013.01); *G01N 33/521* (2013.01); *G01N 2001/007* (2013.01)

(58) Field of Classification Search
CPC ............... B01L 3/5082; G01N 33/521; G01N 2001/007
See application file for complete search history.

(56) References Cited

U.S. PATENT DOCUMENTS

| | | | | |
|---|---|---|---|---|
| 7,618,591 | B2 * | 11/2009 | Slowey | A61B 10/02 422/412 |
| 2001/0039058 | A1 * | 11/2001 | Iheme | G01N 35/1079 436/180 |
| 2004/0161804 | A1 * | 8/2004 | McCash | G01N 33/5695 435/7.2 |
| 2004/0254499 | A1 * | 12/2004 | Smutney | A61B 5/154 600/576 |
| 2005/0013746 | A1 * | 1/2005 | Lee | B01L 3/5082 422/547 |

\* cited by examiner

*Primary Examiner* — Jennifer Wecker
*Assistant Examiner* — Ali Husain Faraz
(74) *Attorney, Agent, or Firm* — Klarquist Sparkman, LLP (57) ABSTRACT

A specimen tube comprises a tubular body having a first end that is open, a second end that is closed and at least one side extending axially between the first end and the second end. The side and the closed end define an interior of the tube. In sonic implementations, the specimen tube comprises a plurality of foot members protruding from the second end of the tube, wherein at least a first foot member and a second foot member have different shapes from each other. In some implementations, at least one internal wall positioned within the interior of the tube defines a sample carrier holding space between at least one surface of the internal wall and an adjacent surface of the side of the tube, the sample carrier holding space being sized to store a swab inserted from the open end of the tube.

20 Claims, 9 Drawing Sheets

SPECIMEN TUBE

BACKGROUND

Specimen tubes are used to contain, transport and store specimens, including specimens of bodily fluids. Testing of specimens from specimen tubes is typically done in batches, and one or more steps of the process may involve automated handling or other automated operations, whereas other steps typically involve manual handling.

Conventional specimen tubes can be difficult to stand upright. It is also sometimes difficult to retrieve a single conventional specimen tube from among a group of specimen tubes in a rack or tray. Also, using an automated capper/decapper apparatus with a conventional specimen tube can be challenging because the torque applied by the apparatus must be resisted. Further, it can be difficult to use conventional specimen tubes to house and provide access to swabs in a ways that promote efficient automated processes. Moreover, it would be helpful to improve current approaches to identifying an individual specimen tube or subset of specimen tubes from a larger group of such tubes, as well as to identify its state or status.

DETAILED DESCRIPTION

A specimen tube suitable for containing a fluid, such as a test specimen (test sample) together with any sample transport medium that may be present, provides for enhanced handling and processing, including manual and automated steps. The specimen tube has feet members to permit it to be stood upright more stably. At least one of the feet members is shaped to engage a recess in a rack or tray to resist torque applied to the specimen tube, e.g., in removing a cap from the specimen tube. The specimen tube may have an internal sample carrier holding space for storing a sample carrier (e.g., a swab or other implement used in collecting a specimen or sample), tending to keep it in a known position within the specimen tube. The sample carrier holding space may have a predetermined position or orientation relative to an exterior feature (e.g., one of the feet members). The specimen tube can have a tactile feature that provides an indication to the user that the cap is fully tightened to prevent overtightening. The specimen tube can be formed of a plastic having irradiation adders, or have a coating or component with irradiation adders or other similar material that permits the specimen tube to be scanned by a machine vision system. Manual or automated handling of the specimen tube is facilitated by one or more pairs of flat surfaces on its exterior.

Figure 1:
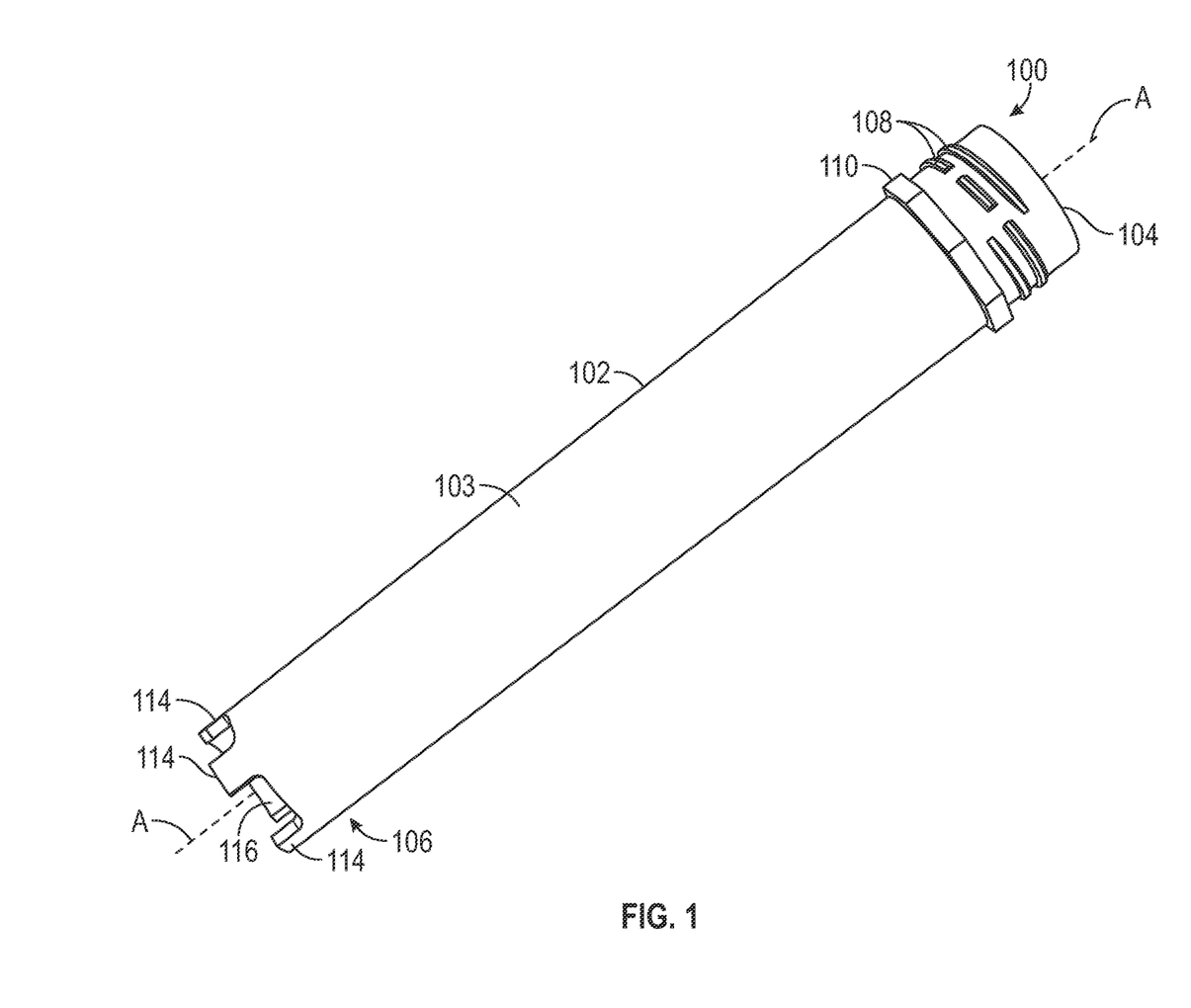
FIG. 1 is a perspective view of a specimen tube.

Referring to FIG. 1, a specimen tube 100 according to a first implementation has an elongate body 102, which is frustoconical in shape with a first open end 104, a second closed end 106 and a side surface that tapers slightly from the open end 104 to the closed end 106. In the illustrated implementation, the body 102 has a circular cross-section, but the body can be formed to have other shapes and cross-sections. As also shown in FIG. 1, the specimen tube 100 has a longitudinal axis A.

The body 102 has one or more external threads 108 positioned adjacent the open end 104. The threads 108 are configured to removably secure a cap (FIG. 17) to the specimen tube 100. In some implementations, the threads 108 are configured as a multi-start thread having multiple thread starts. For example, in the illustrated implementation, a two-start thread is used, which has two thread starts 109 (FIG. 4) arranged at 180 degree intervals from each other. It is also possible to use a three-start thread or a conventional thread. Use of a multi-start thread reduces the number of rotations required to loosen or tighten the cap, which can reduce time, especially in automated processes. Additional details about the threads 108 are described below.

As also shown in FIG. 1, the body 102 has a flange 110 that projects laterally outwards away from an outer surface 103. The flange has at least one opposing pair of flat surfaces 124 (FIG. 16), which are discussed below in more detail.

Figure 2:
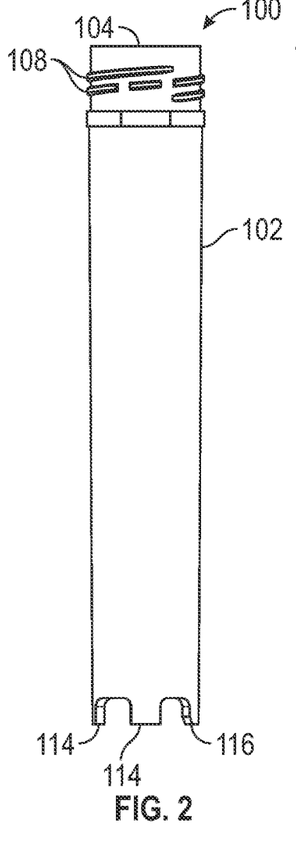
FIGS. 2-6 are front elevation, left side elevation, right side elevation, top plan and bottom plan views of a first implementation of the specimen tube.
Figure 3:
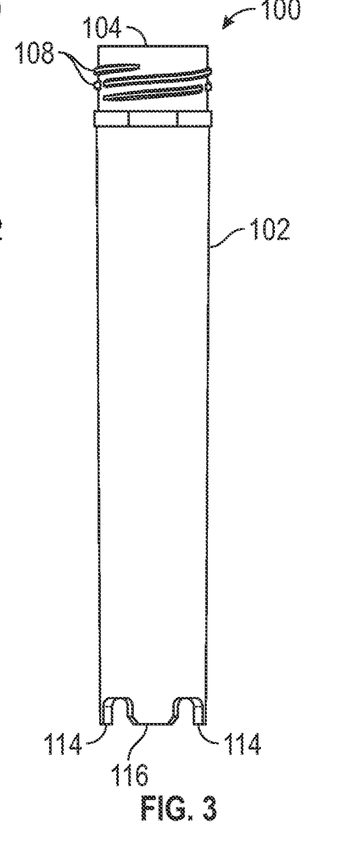
Figure 4:
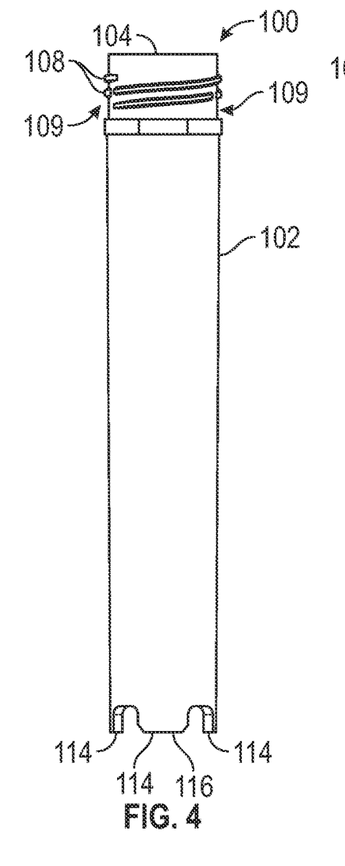
Figure 5:
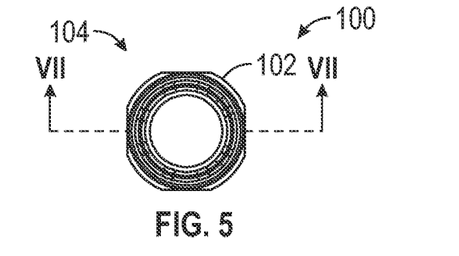
Figure 6:
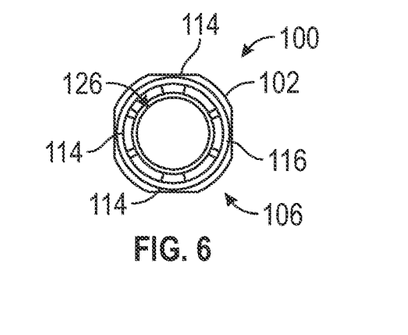
Figure 7:
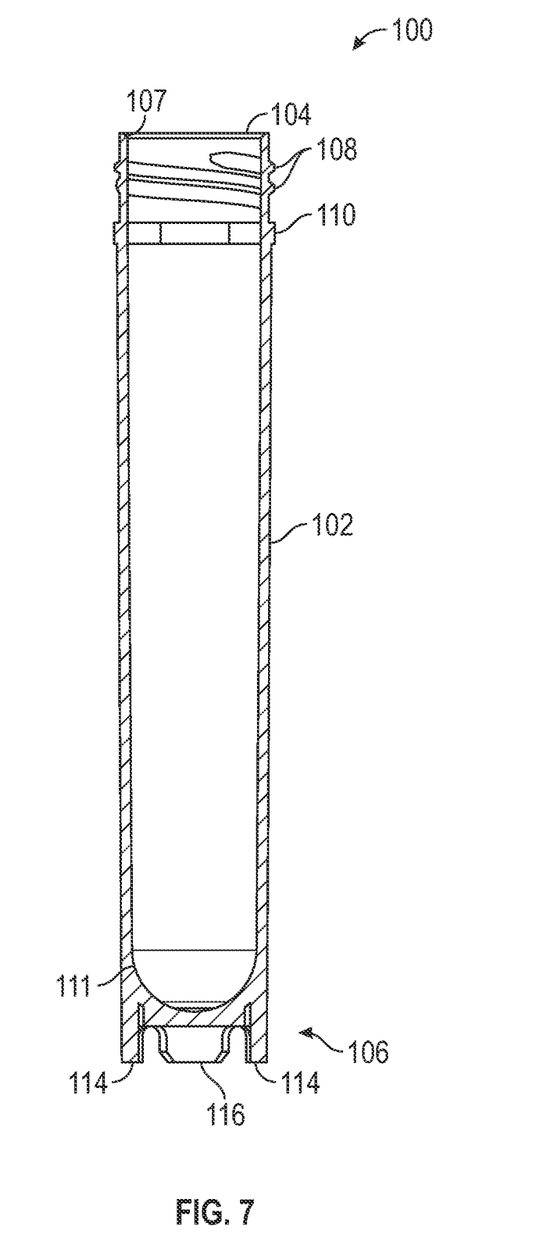
FIG. 7 is section view of the specimen tube taken along the line VII-VII in FIG. 5.
Figure 8:
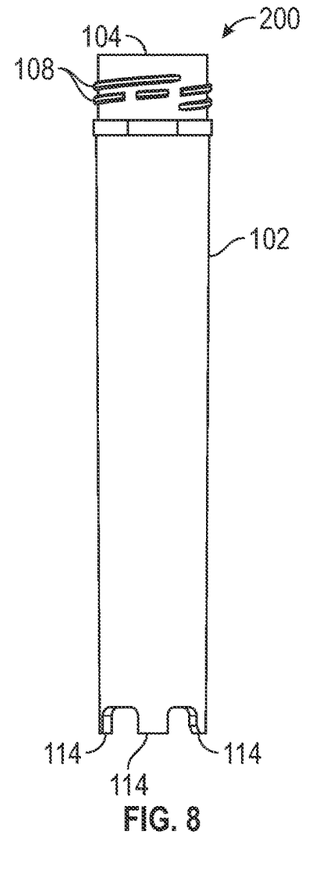
FIGS. 8-12 are front elevation, left side elevation, right side elevation, top plan and bottom plan views of a second implementation of the specimen tube.
Figure 9:
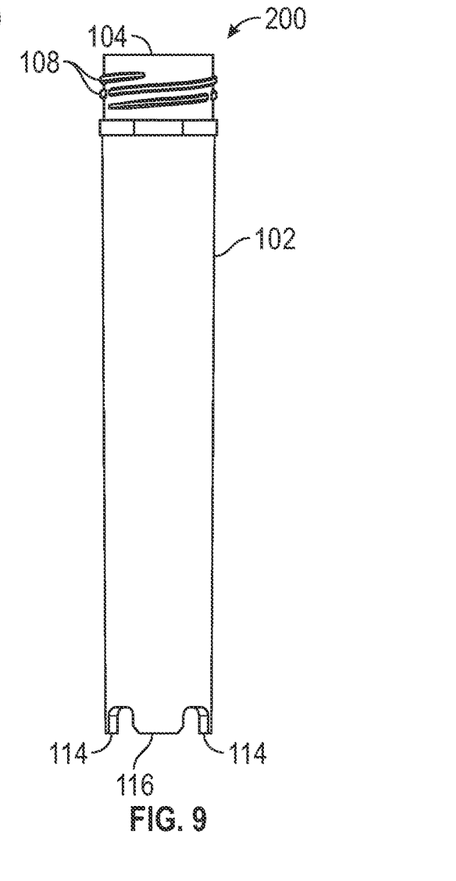
Figure 10:
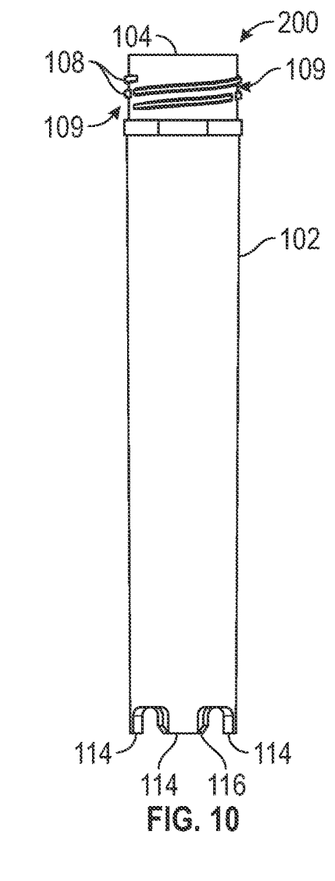

FIGS. 2-4 are front, left and right elevation views of the specimen tube 100, respectively. FIGS. 5 and 6 are respective top plan and bottom plan views. FIG. 7 is a section view in elevation of the specimen tube 100.

As shown in FIGS. 2-7, the closed end 106 has multiple foot members designed to facilitate positioning the specimen tube 100 in an upright position on a level surface (e.g., such as a table or counter). In the illustrated implementation, there are four foot members, including three first foot members 114 and one second foot member 116, that are equally spaced in the circumferential direction. In other implementations, fewer than four foot members or greater than four foot members can be provided.

In the illustrated implementation, the foot members 114, 116 extend axially within the circular cross-section of the body 102, as best shown in FIG. 6. Thus, the foot members do not extend laterally (radially outward) beyond the periphery of the remainder of the body 102. As a result, the foot members 114, 116 do not increase the diameter of the specimen tube 102, and thus ensure it can be used with conventional racks and holders designed to receive specimen tubes having a circular cross-section.

Figure 12:
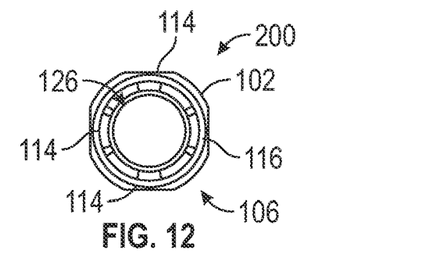
Figure 13:
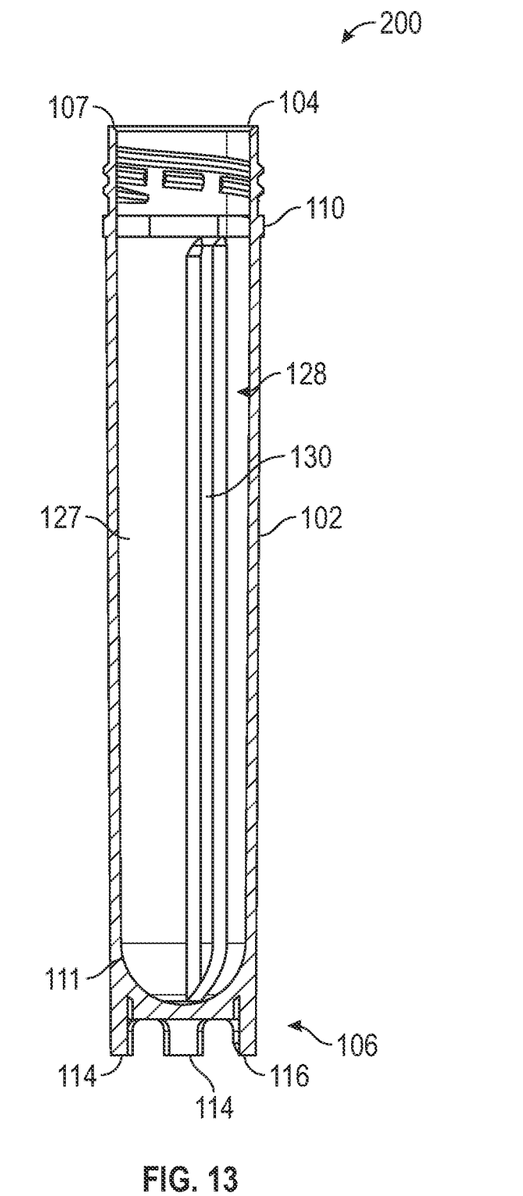
FIG. 13 is section view of the specimen tube taken along the line XIII-XIII in FIG. 11.
Figure 15:
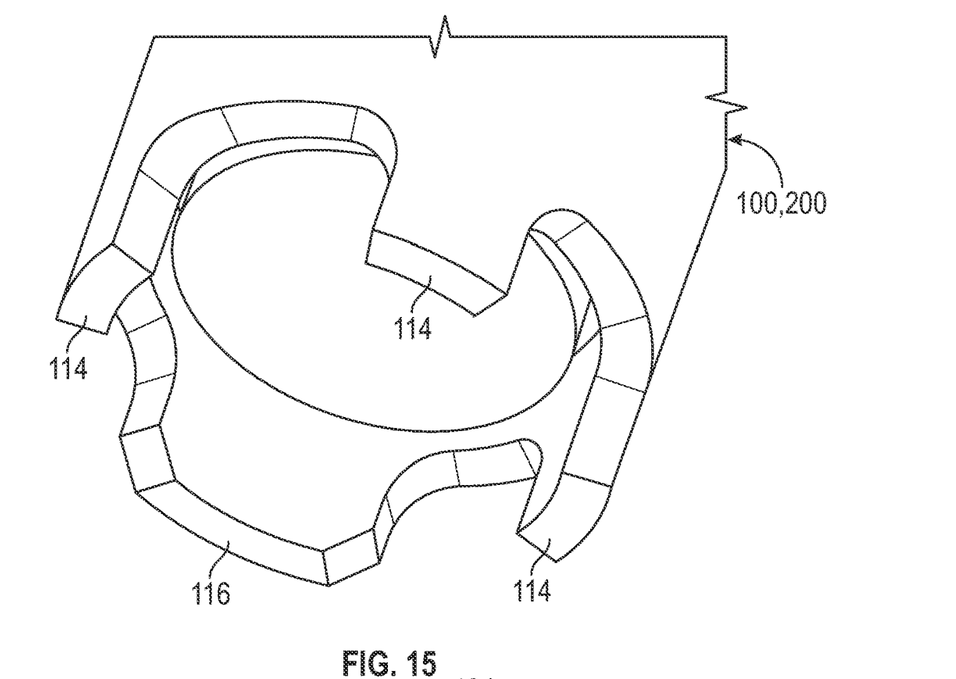
FIG. 15 is a magnified partial perspective view of the second end of the specimen tube.

Also, the foot members 114, 116 configured as shown do not extend into a center base area 126 (see FIGS, 6, 12 and 15), and thus do not impede access to this area, such as for line-of-sight scanning of a bar code, QR code or other encoded information in this area (not shown).

In the illustrated implementation, the multiple foot members have different shapes. For example, at least one foot member, such as the second foot member 116, can have a different shape from other foot members, such as the first foot members 114, As best shown in FIG. 15, in the illustrated implementation, the four foot members are equally spaced (i.e., at 90 degree intervals) but the second foot member 116 has a greater length in the circumferential direction than a length of any of the first foot members 114.

With at least one foot member configured differently from the others, the different foot member can be used as a reference to specify a desired angular position of the specimen tube 100. As one example, the different foot member may be positioned to indicate where a sample carrier and/or its internal holding area (described below) is positioned. For example, a largest foot member could be aligned with (or exactly opposite) a sample carrier and/or sample carrier receiving area.

Also, one or more of the foot members can be engaged with corresponding features (e.g., recesses) in a rack, tray or other device in which the specimen tube 100 is placed. For example, the specimen tube 100 can be used with a multi-position rack, tray or other device (not shown) having only one recess corresponding in size to the second foot member 116 for each position, thereby providing a guide for easily orienting the specimen tube 100 present in that position to a predetermined angular orientation. Thus, a rack or tray for the specimen tube 100 could have 96 specimen tube positions (or other standard number), with each position having four recesses, only one of which is large enough to accommodate the second foot member 116.

In addition, engagement between one or more of the multiple foot members and a receiving structure, such as a rack, tray or other device, allows the specimen tube 100 to resist rotation about its axis from an applied torque, such as a torque applied to the open end 102 to remove a cap or to install a cap by rotation. Such engagement can be also help keep the specimen tube in place by resisting undesired axial movement, e.g., during removal of a specimen tube cap.

As best shown in FIG. 7, the specimen tube 100 can have a bowl-shaped interior end surface 111 defined adjacent the closed end 106, which tends to promote easier withdrawal of fluids from the specimen tube 100. As also shown in FIG. 7, the specimen tube 100 can have a end surface formed with a chamfer 107 or curve.

Figure 11:
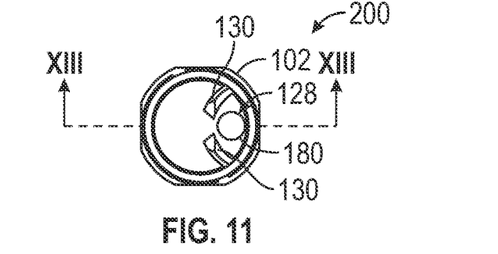
Figure 14:
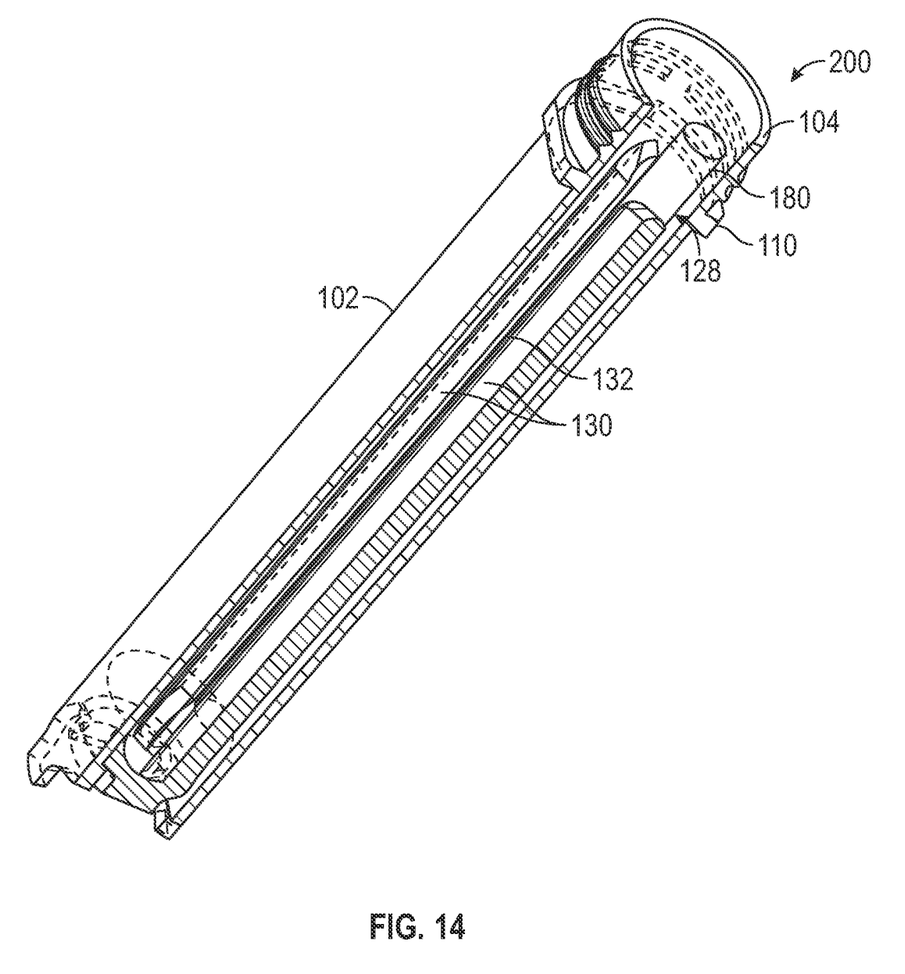
FIG. 14 is a sectioned perspective view of the second implementation of the specimen tube.

In some implementations, the specimen tube is configured to have a holding space for a sample carrier or tool within the interior of the specimen tube. For example, as shown in FIGS. 8-14, a specimen tube 200 according to a second implementation has a sample carrier holding space 128 defined between at least one internal wall and an inner surface of the specimen tube. In other respects, the specimen tube 200 is similar to the specimen tube 100, and the same reference numerals are used. As best shown in FIGS. 11 and 14, there are two walls 130 that extend generally radially inward from the inner surface 127 to define the sample carrier holding space 128 therebetween. In FIG. 11, an end of a representative sample carrier 180 is visible between the walls 130. In the sectioned perspective view of FIG. 14, it can be seen that the walls 130 extend over a majority of the length of the body 102 but allow a portion of the sample carrier 180 to protrude so that it can be accessed through the open end.

The sample carrier 180 may be any implement or tool used to gather a specimen or sample, or to transfer a specimen or sample to or from the specimen tube to another location. For example, the sample carrier 180 may be a swab, a brush, a needle, a scraper or other implement suitable for retrieving a specimen or sample, and may have a generally elongate shape.

In the illustrated implementation, the wails 130 are separated from each other by a gap 132. The gap 132 allows for fluid communication between the sample carrier holding area and the rest of the interior. Other configurations, such as a continuous wall or walls provided with an opening, are also possible.

In some implementations, the wall or walls 130 extend over a length sufficient to serve as a fulcrum for breaking off a portion of the shaft of the sample carrier 180 so that the remaining portion can be fully accommodated within the specimen tube. To break off a length of the sample carrier, the user inserts it partway into the sample carrier holding space 128, and then flexes the shaft against the upper end 104 while the tip contacts the wall(s) 130 until the shaft breaks.

The sample carrier holding space 128 is sized to still permit access to a remainder of the interior of the specimen tube, including for aspiration of specimen or sample with an appropriate tip. Also, the wall(s) 130 separating the sample carrier 180 from any such tip inserted into the specimen tube tend to prevent the sample carrier 180 from being inadvertently removed from the specimen tube. such as if it adheres to or wicks against the tip as it is withdrawn.

In some implementations, the sample carrier holding space 128 is defined without walls, and may optionally include a retainer or an alignment mechanism.

Figure 16:
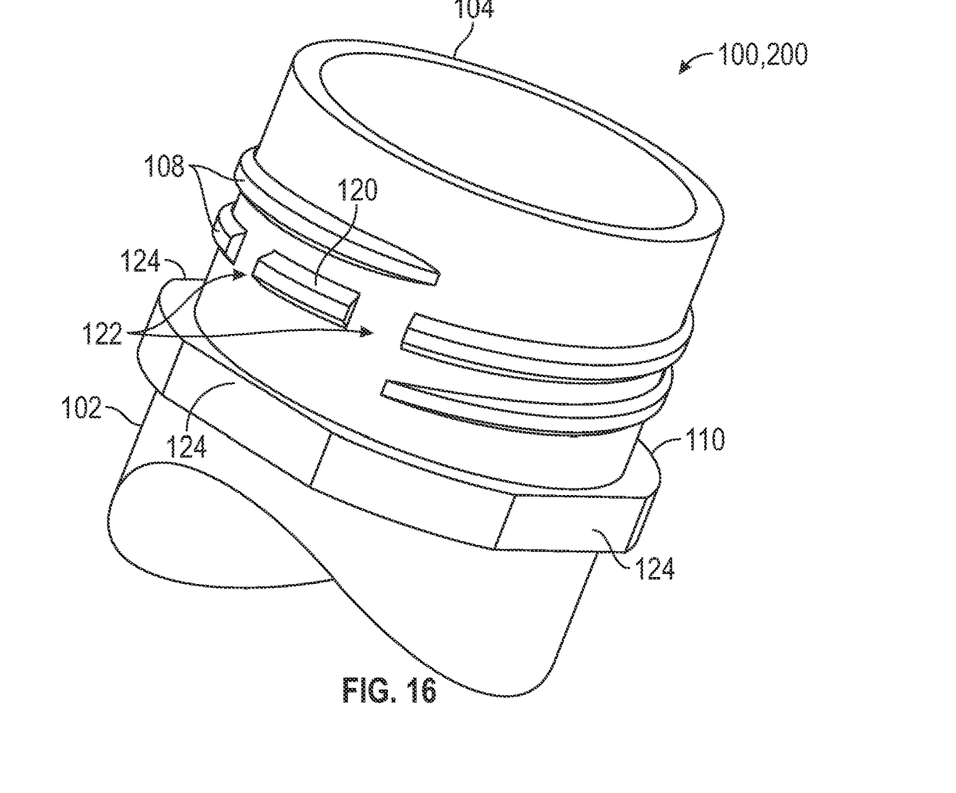
FIG. 16 is a magnified partial perspective view of the first end of the specimen tube.

FIG. 16 is a magnified view of the open end 104 of the specimen tube 100, 200. As described, the flange 110 is preferably provided with at least one pair of opposing flat surfaces 124, 124. In the illustrated implementation, there are two pairs of opposing flat surfaces 124, 124. The flat surfaces 124, 124 allow the specimen tube 100, 200 to be grasped by tweezers or an automated gripping device (whether under control by an operator or operating autonomously). The orientation of each pair of flat surfaces 124, 124 can be set to allow accessing one specimen tube from among a rack or tray with multiple specimen tubes packed closely together. Also, the geometry of the flange 110 and/or the flat surfaces 124, 124 allows the specimen tube 100, 200 to manipulated in automated processes that use gripping devices that contact external surfaces, which reduces risks of contamination.

FIG. 16 also shows the threads 108 in greater detail. As described above, the specimen tube 100, 200 can be provided with any suitable form of threads or other finish for removably securing a specimen tube cap. According to the illustrated implementation, the threads 108 may include one or more interrupted threads 120 with gaps 122. at predetermined intervals. The gaps 122 can provide for easier release of the specimen tube from a molding tool. In addition, the gaps may provide a path for releasing pressure from the interior of the specimen tube 100, 200 (such as may be produced over time due to changes in ambient temperature and/or pressure, etc.) as the cap is loosened. Releasing pressure through the gaps 122 is a more controllable process and tends to cause less specimen and/or other fluid to be expelled unintentionally.

Figure 17:
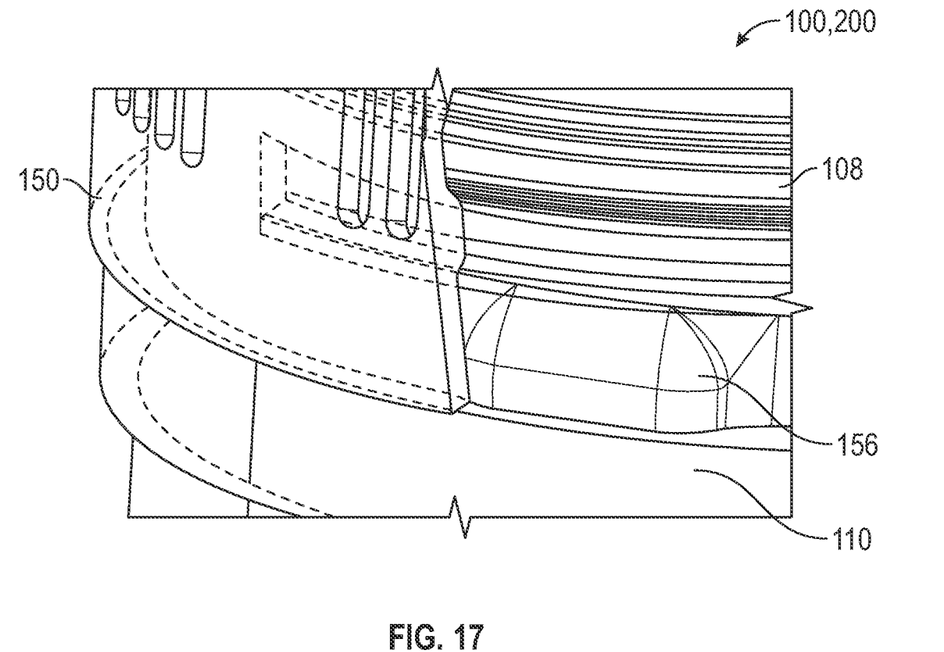
FIG. 17 is a perspective view of a portion of the specimen tube in relation to a cap, which is partially shown, to reveal an indicator feature on the specimen tube.
Figure 18:
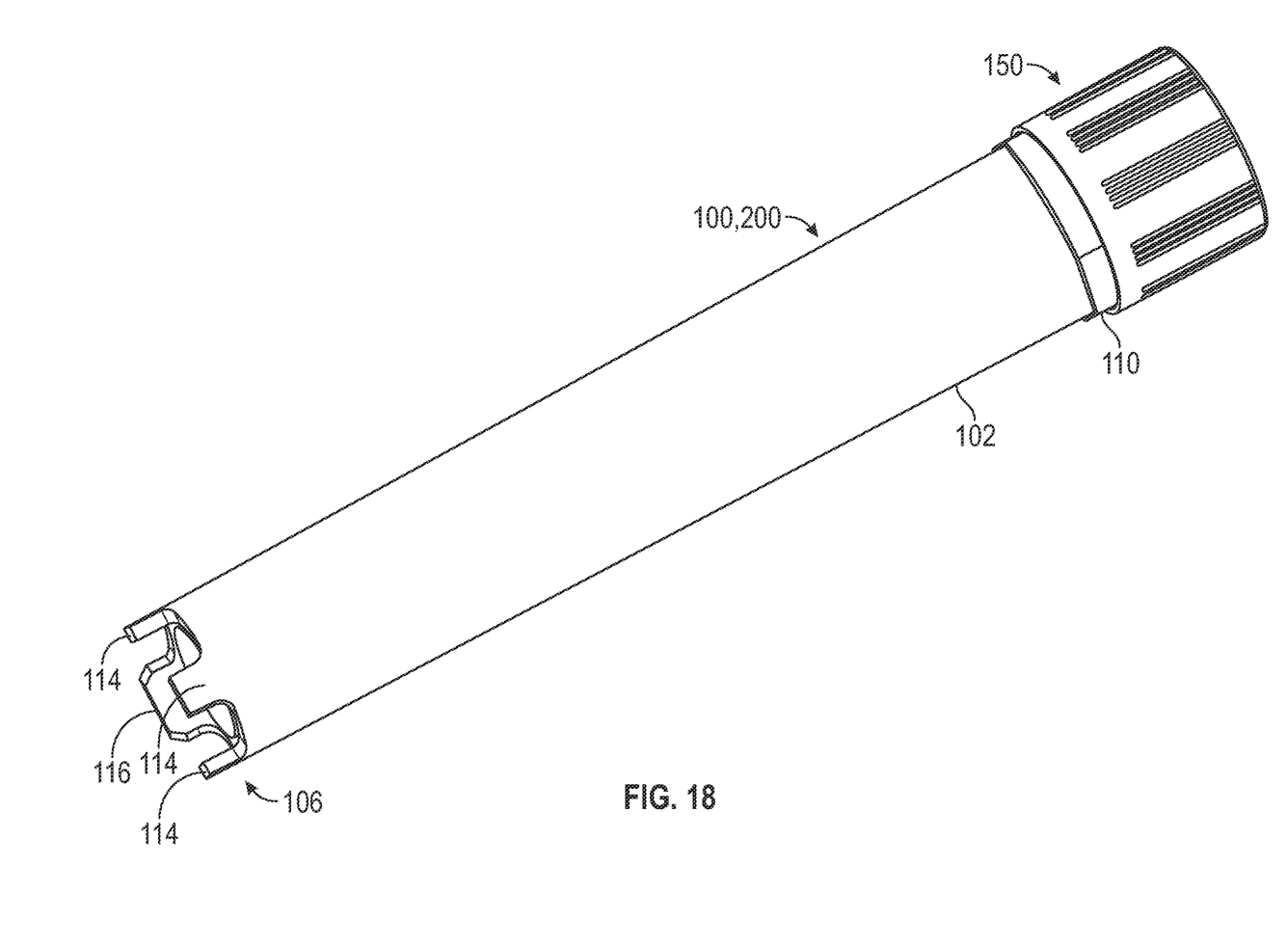
FIG. 18 is a perspective view of the specimen tube assembled with a specimen tube cap.

FIG. 17 is a perspective view showing a portion of the specimen tube 100, 200 provided. with an indicator 156 configured to provide a. user with a. tactile and/or audible indication that a cap 150 (shown partially) has reached a predetermined position, e.g., that it is fully threaded and/or secured. The indicator 156 may be shaped as a protrusion adjacent the flange 110 as shown. The indicator 156 may cooperate with a corresponding protrusion or recess formed in the cap (not shown). Similarly, the indicator 156 may be shaped as a recess (not shown) instead of as a protrusion to interact with a protrusion on the cap. When the cap reaches a predetermined position, engagement with the indicator 156 causes a tactile sensation and/or a sound that can signal a user. One or more markings can also be added to provide a visual indication to the user of the position of the cap relative to one or predetermined positions, including a full tightened position.

The specimen tube can be configured to have similar dimensions to conventional specimen tubes, such as a 1.0 mL specimen tube, as well as smaller or larger tubes from about 0.5 mL to about 5.0 mL. The specimen tube can be made to have an external diameter compatible with existing equipment, such as racks, trays and apparatus. It is also possible to configure the specimen tube to have a customized geometry-, e.g., with a different diameter, wall thickness and/or height.

The specimen tube can be made of any suitable material, including, e.g., a plastic material. Suitable plastic materials include polypropylene, polycarbonate, polyethylene and/or blends thereof In some implementations, the specimen tube may be assembled together from separate components made of two or more different materials. The specimen tube can be formed by methods such as injection molding, blow molding and other suitable methods.

In some implementations, the specimen tube has at least one area that is configured to have a different color than other areas. In some implementations, the specimen tube is configured to be identifiable by a scanning system used in tracking specimen tubes as they are stored and manipulated. In some implementations, the specimen tube is made trackable by configuring it for use in a machine vision system. For example, the specimen tube can have a tag or the material(s) with which it is coated or made can have special ingredients, such as irradiation adders, that cause the specimen tube to be florescent under predetermined conditions. Other scanning technologies can also be used.

The specimen tube can have an outer surface that is treated or otherwise configured to make it easier to handle, such as by users wearing gloves. For example, the outer surface can be provided with ridges to help prevent the adhesion that can tend to occur between plastic and the user's fingers. Also, a plastic material treated to tend to weaken any static attraction or other "stickiness" present between the plastic material and the user's fingers can be used.

In view of the many possible embodiments to which the disclosed principles may be applied, it should be recognized that the illustrated embodiments are only examples and should not be taken as limiting the scope. I therefore claim as my invention all that comes within the scope of these claims.

What is claimed is:

1. A specimen tube, comprising:
   a tubular body extending longitudinally and having a first end that is open, a second end that is dosed and at least one side extending longitudinally between the first end and the second end, wherein an inner surface of the at least one side and an inner surface of the second end define an interior of the specimen tube;
   a plurality of foot members protruding from the second end of the specimen tube, wherein at least a first foot member and a second foot member have different shapes from each other configured to indicate an angular orientation relative to a longitudinal axis of the specimen tube; and
   at least one internal wall projecting inwardly from the inner surface of the at least one side and extending longitudinally, the internal wall and an adjacent portion of the inner surface of the at least one side defining a sample carrier holding space, the sample carrier holding space being sized to store a sample carrier inserted from the first end of the specimen tube and having a predetermined angular position relative to one of the plurality of foot members.

2. The specimen tube of claim 1, wherein the plurality of foot members comprises the first foot member, the second foot member and two additional second foot members that are equally spaced about a central axis of the specimen tube, and wherein the first foot member is aligned with the sample carrier holding space.

3. The specimen tube of claim 1, wherein at least one of the first foot member and the second foot member is shaped to engage a recess in a tray or a rack to hold the second end of the specimen tube in place and counteract a torque applied to a first end of the specimen tube.

4. The specimen tube of claim 1, wherein the foot members are shaped to facilitate positioning the specimen tube in an upright position on a level surface.

5. The specimen tube of claim 1, wherein the foot members do not extend radially outward beyond the at least one side of the tubular body.

6. The specimen tube of claim 1, further comprising an external thread adjacent the first end and configured to receive a specimen tube cap, wherein the external thread comprises a multi-start thread.

7. The specimen tube of claim 1, wherein the specimen tube is formed of a plastic comprising irradiation adders suitable to permit identification of the specimen tube by machine vision scanning.

8. A specimen tube, comprising:
   a tubular body having a first end that is open, a second end that is closed and at least one side extending longitudinally between the first end and the second end, wherein an inner surface of the at least one side and an inner surface of the second end define an interior of the specimen tube;
   an external thread on the first end configured to receive a specimen tube cap; and
   a sample carrier holding space defined within the interior of the specimen tube adjacent the inner surface of the at least one side and a facing surface of an internal wall projecting inwardly from the inner surface of the at least one side and extending longitudinally, the sample carrier holding space being sized to receive an uprightly positioned sample carrier, wherein the sample carrier holding space is positioned at a predetermined angular orientation relative to an exterior feature of the tubular body.

9. The specimen tube of claim 8, wherein the tubular body comprises a plurality of foot members protruding from the second end of the specimen tube, the plurality of foot members comprising at least one differently-shaped foot member that is shaped differently than other foot members, and wherein the predetermined angular orientation of the sample carrier holding space is relative to the at least one differently-shaped foot member.

10. The specimen tube of claim 8, wherein the specimen tube is formed of a plastic comprising irradiation adders.

11. A specimen tube, comprising:
   a tubular body having a first end that is open, a second end that is dosed and at least one side extending longitudinally between the first end and the second end, wherein an inner surface of the at least one side and an inner surface of the second end define an interior of the specimen tube;
   an external thread on the first end configured to receive a specimen tube cap; and at least one internal wall projecting inwardly from the inner surface of the at least one side and extending longitudinally, the inner surface of the at least one side and a facing surface of the internal wall defining a sample carrier holding space, the sample carrier holding space having a cross sectional area less than a cross sectional area of the interior and being sized to store a sample carrier inserted from the first end of the specimen tube.

12. The specimen tube of claim 11, wherein the at least one internal wall is positioned within the interior to define a fulcrum against which an elongate sample carrier comprising an elongate implement inserted at least partially into the sample carrier holding space can be flexed to break off a shaft of the elongate implement.

13. The specimen tube of claim 11, wherein the at least one internal wall is a first internal wall, further comprising a second internal wall separated from the first internal wall by a gap, and wherein the sample carrier holding space is defined between the facing surface of the first internal grail, a facing surface of the second internal wall and the inner surface of the at least one side.

14. The specimen tube of claim 13, wherein the first internal wall and the second internal wall extend generally radially and are curved when viewed along a longitudinal axis of the specimen tube.

15. The specimen tube of claim 11, wherein the sample carrier holding space and a specimen space are in fluid communication with each other.

16. The specimen tube of claim 11, further comprising a plurality of foot members protruding from the second end of the specimen tube, wherein at least a first foot member and a second foot member have different shapes from each other.

17. The specimen tube of claim 11, further comprising a flange projecting outwardly from the tubular body, the flange comprising at least one pair of opposing flat sides shaped to facilitate gripping of the specimen tube.

18. The specimen tube of claim 11, wherein the external thread comprises a multi-start thread.

19. The specimen tube of claim 11, wherein the specimen tube is formed of a plastic comprising irradiation adders.

20. The specimen tube of claim 1, wherein the at least one internal wall is a first internal wall, further comprising a second internal wall protruding inwardly from the inner surface of the at least one side at an angularly spaced location relative to the first internal wall, wherein the first internal wall, the second internal wall and an adjacent portion of the inner surface of the at least one side define the sample carrier holding space, wherein the first internal wall has a radially inner first free end and the second internal wall has a radially inner second free end, wherein the first free end and the second free end oppose each other and are spaced apart to define a gap in the sample carrier holding space.

* * * * *

UNITED STATES PATENT AND TRADEMARK OFFICE
CERTIFICATE OF CORRECTION

| | |
|---|---|
| PATENT NO. | : 11,845,082 B1 |
| APPLICATION NO. | : 17/212905 |
| DATED | : December 19, 2023 |
| INVENTOR(S) | : Justinn Eddie |

It is certified that error appears in the above-identified patent and that said Letters Patent is hereby corrected as shown below:

In the Claims

Column 5, Line 52, "that is dosed" should read -- that is closed --.

Column 6, Line 61, "that is dosed" should read -- that is closed --.

Signed and Sealed this
Twenty-seventh Day of February, 2024

Katherine Kelly Vidal
*Director of the United States Patent and Trademark Office*